US008222008B2

(12) United States Patent
Thoene

(10) Patent No.: US 8,222,008 B2
(45) Date of Patent: Jul. 17, 2012

(54) METHODS AND COMPOSITIONS FOR TREATING CANCER

(75) Inventor: Jess G. Thoene, Ann Arbor, MI (US)

(73) Assignee: The Administrators of The Tulane Educational Fund, New Orleans, LA (US)

( * ) Notice: Subject to any disclaimer, the term of this patent is extended or adjusted under 35 U.S.C. 154(b) by 509 days.

(21) Appl. No.: 12/430,964

(22) Filed: Apr. 28, 2009

(65) Prior Publication Data

US 2009/0227676 A1 Sep. 10, 2009

Related U.S. Application Data

(62) Division of application No. 10/575,938, filed as application No. PCT/US2004/032305 on Oct. 15, 2004, now abandoned.

(60) Provisional application No. 60/511,922, filed on Oct. 16, 2003.

(51) Int. Cl.
| | | |
|---|---|---|
| *C12P 13/12* | (2006.01) | |
| *A61K 38/05* | (2006.01) | |
| *A61P 35/00* | (2006.01) | |
| *G01N 33/574* | (2006.01) | |
| *C12N 5/09* | (2010.01) | |

(52) U.S. Cl. .................... 435/113; 514/21.91; 435/7.23; 435/344

(58) Field of Classification Search ........................ None
See application file for complete search history.

(56) References Cited

U.S. PATENT DOCUMENTS

2007/0078093 A1 4/2007 Thoene

FOREIGN PATENT DOCUMENTS

| EP | 1364943 A1 * | 11/2003 |
|---|---|---|
| WO | WO 02/051405 * | 7/2002 |
| WO | WO-2005-039490 | 5/2005 |

OTHER PUBLICATIONS

Afford, "Demystified . . . Apoptosis", J. Clin. Pathol. Mol. Pathol., 53:55-63 (Apr. 2000).
Bajaj, "Proximal tubule dysfunction in cystine-loaded tubules: effect of phosphate and metabolic substrates", Am. J. Physiol., 271(3 Pt 2):F717-22 (Sep. 1996).
Ben-Nun, "Cystine loading induces Fanconi's syndrome in rats: in vivo and vesicle studies", Am. J. Physiol., 265(6 Pt 2):F839-44 (Dec. 1993).
Buschini, "*Saccharomyces cerevisiae* as an Eukaryotic Cell Model to Assess Cytotoxicity and Genotoxicity of Three Anticancer Anthraquinones", Mutagenesis, 18(1):25-36 (Jan. 2003).
Coleman, "Membrane Blebbing During Apoptosis Results from Caspase-Mediated Activation of Rock I", Nature Cell Biol., 3:339 (Apr. 2001).
Cherqui, "Intralysosomal Cystine Accumulation in Mice Lacking Cystinosin, the Protein Defective in Cystinosis", Mol. Cell. Biol., 22(21):7622-7632 (Nov. 2002).
Chu, "PKC Isozyme S-cysteinylation by Cystine Stimulates the Pro-Apoptotic Isozyme PKCδ and Inactivates the Ocogenic Isozyme PKCε", Carcinogenesis, 24(2):317-325 (Feb. 2003).
Chu, "Cellular Protein Kinase C Isozyme Regulation by Exogenously Delivered Physiological Disulfides-Implications of Oxidative Protein Kinase C Regulation to Cancer Prevention", Carcinogenesis, 25(4):585-596 (Apr. 2004; E Pub: Dec. 4, 2003).
De Jong, "Inhibition of renal uptake of indium-111-DTPA-octreotide in vivo", J. Nucl. Med., 37(8):1388-92 (Aug. 1996).
Helip-Wooley, "Expression of CTNS Alleles: Subcellular Localization and Aminoglycoside Correction in Vitro", Mol. Genetics and Metabol., 75:128-133 (Feb. 2002).
Kanduc, "Cell Death: Apoptosis Versus Necrosis (Review)", Int. J. Oncol., 21:165-170 (Jul. 2002).
Kang, "A Role for Uric Acid in the Progression of Renal Disease", J. Am. Soc. Nephrol., 13:2888-2897 (Dec. 2002).
Kaufmann, "Induction of Apoptosis by Cancer Chemotherapy", Exp. Cell. Res., 256:42-49 (Apr. 10, 2000).
Kitazawa, "Intracellular redox regulation by a cystine derivative suppresses UV-induced NF-K B activation", FEBS Letters, 526(1-3):106-110 (Aug. 28, 2002).
Lemons, "Elevated Temperature Produces Cystine Depletion of Cystinotic Fibroblasts", Biochim. et Biophys. Acta, 884:429-434 (Dec. 10, 1986).
McIntyre, "Butyrate production from dietary fibre and protection against large bowel cancer in a rat model", Gut, 34(3):386-91 (Mar. 1993).
Oiry, "Synthesis and Radioprotective Activity of Dipeptide Cysteamine and Cystamine Derivatives", J. Med. Chem., 32:297-301 (Feb. 1989).
Oshima, "Cystine Metabolism in Human Fibroblasts", J. Biol. Chem., 251(14):4287-4293 (Jul. 25, 1976).
Park, "Cystinotic Fibroblasts Display Aberrant Apoptosis", Am. J. Hum. Genetics, 69(4), Abstract 1774 (Oct. 2001).
Park, "Potential Role of Apoptosis in Development of the Cystinotic Phenotype", Pediatr. Nephrol., 20:441-446 (Apr. 2005—E Pub: Dec. 28, 2004).
Park, "Lysosomal Cystine Storage Augments Apoptosis in Cultured Human Fibroblasts and Renal Tubular Epithelial Cells", J. Am. Soc. Nephrol., 13:2878-2887 (Dec. 2002).
Park, "Mouse L929 Fibroblasts do not Display Increased Apoptosis Following Lysosomal Cystine Loading with CDME", American Society of Human Genetics, 53rd Annual Meeting, Los Angeles, CA, Biochemical Genetics Poster #42 (Nov. 4-8, 2003).
Pellett, "Renal Cell Culture Using Autopsy Material from Children with Cystinosis", In Vitro, 20(1):53-58 (Jan. 1984).
Pisoni, "Utilization of Mercaptoethylgluconamide for Depleting Human Cystinotic Fibroblasts of their Accumulated Lysosomal Cystine", Pediatric Research, 26(1): 73-76 (Jul. 1989).

(Continued)

*Primary Examiner* — Cecilia J Tsang
*Assistant Examiner* — Satyanarayana R Gudibande
(74) *Attorney, Agent, or Firm* — Howson & Howson LLP

(57) ABSTRACT

Pharmaceutical compositions and kits useful for the treatment of cancer include certain alkyl esters of cystine and certain alkyl-substituted cystamine derived esters, including, for example, cystine dimethyl ester and a di-alkyl peptidyl cystamine ester, among others. These compounds may be employed in methods of treating cancers or methods of determining sensitivity of certain cancer cells to apoptosis alone, or in combination with other chemotherapeutic, radiological or apoptotic agents.

11 Claims, 4 Drawing Sheets

OTHER PUBLICATIONS

Pisoni, "Detection and Characterization of a Transport System Mediating Cysteamine Entry into Human Fibroblast Lysosomes", J. Biol. Chem., 270(3):1179-1184 (Jan. 20, 1995).

Pisoni, "Important Differences in Cationic Amino Acid Transport by Lysosomal System c and System $y^+$ of the Human Fibroblast", J. Biol. Chem., 262(31):15011-15018 (Nov. 5, 1987).

Pisoni, "Detection and Characterization of Carrier-Mediated Cationic Amino Acid Transport in Lysosomes of Normal and Cystinotic Human Fibroblasts", J. Biol. Chem., 260(8):4791-4798 (Apr. 25, 1985).

Pisoni, "Description of a Selection Method Highly Cytotoxic for Cystinotic Fibroblasts but not Normal Human Fibroblasts", Somatic Cell Molecular Genetics, 18(1):1-6 (Jan. 1992).

Sauter, "Consequences of Cell Death: Exposure to Necrotic Tumor Cells, but Not Primary Tissue Cells or Apoptotic Cells, Induces the Maturation of Immunostimulatory Dendritic Cells", J. Exp. Med., 191(3):423 (Feb. 7, 2000).

Schneider, "Ineffectiveness of Ascorbic Acid Therapy in Nephropathic Cystinosis", N. Engl. J. Med., 300:756 (Apr. 5, 1979).

Shiokawa, "Involvement of DNase γ in Apoptosis Associated with Myogenic Differentiation of C2C12 Cells", J. Biol. Chem., 277(34):31031-31037 (Aug. 23, 2002).

Smith, "Lysosomal Cystine Transport", J. Biol. Chem:, 262(3):1244-1253 (Jan. 25, 1987).

Thoene, "Advances in Understanding the Pathophysiology of Cystinosis and Lysosomal Biogenesis", Cystinosis Research Network Newsletter, (Fall 2003).

Thoene, "Mutations of CTNS Causing Intermediate Cystinosis", Mol. Genetics Metabol., 67:283-293 (Aug. 1999).

Thoene, "Cystine Depletion of Cystinotic Cells by Aminothiols", Proc. Roy. Soc. Med., 70(3):37-40 (Jan. 1977).

Thoene, "Inhibitors of Protein Synthesis Also Inhibit Lysosomal Proteolysis Studies Using Cystinotic Fibroblasts", J. Clin. Invest., 75:370-376 (Feb. 1985).

Thoene, "Cystine Accumulation in Cystinotic Fibroblasts from Free and Protein-Linked Cystine but not Cysteine", Biochem. J., 208:823-830 (Dec. 15, 1982).

Thoene, "Cystinotic Fibroblasts Accumulate Cystine from Intracellular Protein Degradation", Proc. Natl. Acad. Sci. USA, 74(10):4504-4507 (Oct. 1977).

Thoene, "Modulation of the Intracellular Cystine Content of Cystinotic Fibroblasts by Extracellular Albumin", Pedatr. Res., 14:785-787 (Jun. 1980).

Thoene, "Cystine Depletion of Cystinotic Tissues by Phosphocysteamine (WR638)", J. Pediatr., 96(6):1043 (Jun. 1980).

Thoene, "Lysosomal Cystine Augmentation of Apoptosis to Treat Cancer", Tulane Cancer Center's Inaugural Mauvernay Research Excellence Seminar and Award Presentation (Oct. 17, 2003).

Thoene, "Cystinosis Intracellular Cystine Depletion by Aminothiols in Vitro and in Vivo", J. Clin. Invest., 58:180-189 (Jul. 1976).

Wittwer, "Metabolism of Pantethine in Cystinosis", J. Clin. Invest., 76:1665-1672 (Oct. 1985).

http://en.wikipedia.org/wiki/indium, 6 pages Retrieved Dec. 10, 2008 (cited by the Examiner in U.S. Appl. No. 10/575,938 in the Notice of References Cited dated Dec. 23, 2008).

* cited by examiner

| Treatment Compound | % Apoptosis | Compound Structure |
|---|---|---|
| Control | 5.3 | -- |
| Cystine | 8.3 | 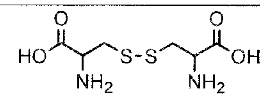 |
| Cystine Dimethylester (CDME) | 39.7 | 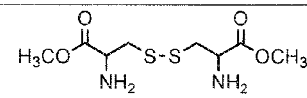 |
| Cystamine | 5.0 | 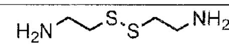 |
| Djenkolic Acid | 5.8 | 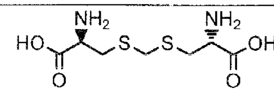 |
| Djenkolic Acid Dimethylester (DKADME) | 6.0 | 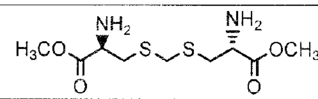 |
| Penicillimine Disulfide | 4.5 | 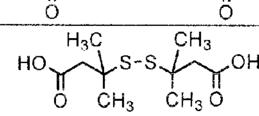 |
| Penicillimine Disulfide Dimethylester (PDDME) | 5.8 | 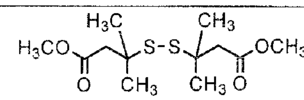 |
| Cys-Ala Disulfide | 5.1 | 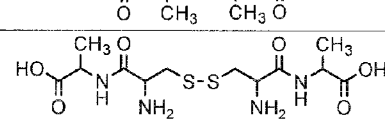 |
| Cys-Ala Disulfide Dimethylester (CADME) | 4.8 | 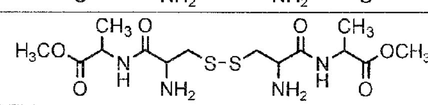 |
| Cys-Gly Disulfide | 4.4 | 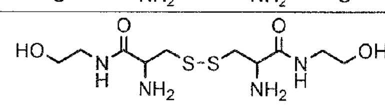 |
| Cys-Gly Disulfide Dimethylester (CGDME) | 7.4 | 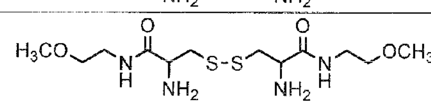 |
| Cys-Val Disulfide | 6.3 | 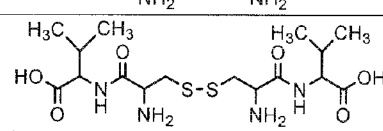 |
| Cys-Val Disulfide Dimethylester (CVDME) | 4.5 | 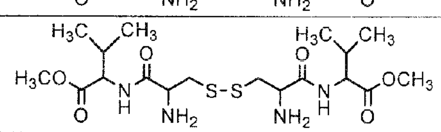 |

Fig. 2

METHODS AND COMPOSITIONS FOR TREATING CANCER

CROSS REFERENCE TO RELATED APPLICATIONS

This application is divisional of U.S. patent application Ser. No. 10/575,938, filed Apr. 13, 2006, which is a national stage of International Patent Application No. PCT/US2004/032305, filed Oct. 15, 2004, which claims the benefit of the priority of U.S. Provisional Patent Application No. 60/511,922, filed Oct. 16, 2003, now abandoned.

BACKGROUND OF THE INVENTION

Apoptosis, or programmed cell death, is a naturally occurring process that has been strongly conserved during evolution to prevent uncontrolled cell proliferation. This form of cell suicide plays a critical role in ensuring the development and maintenance of multicellular organisms by eliminating superfluous or unwanted cells. Insufficient apoptosis, triggered by growth factors, extracellular matrix changes, CD40 ligand, viral gene products, neutral amino acids, zinc, estrogen, and androgens, can contribute to the development of cancer (Afford and Randhawa, Mol. Pathol., 2000, 53, 55-63).

Current treatments for cancer are centered on chemotherapeutic agents and radiation therapy. The goal of these two regimens is usually considered to be the killing of rapidly dividing cells by interfering with processes involved in the replication of cells. These treatments exploit the susceptibility of dividing cells to certain agents. Some of these methods include treatments designed to damage microtubule assembly during mitosis such as colchicine and paclitaxel (Kaufmann and Earnshaw, Experimental Cell Research, 2000, vol. 256, pp. 42-49). Other chemotherapeutic drugs that interfere with the replication of DNA such as doxorubicin and epirubicin (Buschini, et al., Mutagenesis, 2003, vol. 18, no. 1, pp. 25-36).

While these current therapies are targeted to cancerous cells, they have similar effects on otherwise healthy cells involved in the cell division process. There remains a need in the art for compounds and pharmaceutical compositions and methods useful for treatment, prevention and diagnosis of a variety of cancers.

SUMMARY OF THE INVENTION

In one aspect, the present invention provides a pharmaceutical composition useful for the treatment of cancer which includes a compound which is a di-alkyl ester based on cystine as defined by formula (a) below or a compound which is di-alkyl peptidyl cystamine ester of formula (b) below, or a pharmaceutically acceptable salt thereof in a pharmaceutically acceptable carrier. In one embodiment, the compound of formula (a) is cystine dimethyl ester. In one embodiment, the compound of formula (b) is an aspartyl-cystamine dimethyl ester. In still another embodiment, the composition contains a compound of formula (a) and a compound of formula (b). In another embodiment, the composition further contains an additional compound, which is a chemotherapeutic compound or an apoptogen. This composition can contain other pharmaceutically acceptable components for enhancing the penetration of the compound into a cell and/or for extending its bioavailability and increasing its resistance to enzymatic degradation in vivo. A variety of additional embodiments of compounds of the formulae, as well as the definitions for the variable groups in the formula (a) and (b), are disclosed in the detailed description. Such compositions are useful in the treatment, prophylaxis and diagnosis of various cancers. These compounds specifically enhance the sensitivity of target cells to apoptosis alone or with other apoptogenic compounds, and provide compositions and methods for more effective therapies for a variety of cancers.

In another aspect, the invention provides a method of treating or preventing the development of cancer in a mammalian subject by treating cancer cells of the subject with a composition as described herein. The treatment step may be in vivo or ex vivo.

In still another aspect, the invention provides a method for treating or preventing the development of cancer in a mammalian subject by treating said subject, or exposing said subject to, a second chemotherapeutic or apoptogenic agent in addition to the treatment with a composition of this invention. In one embodiment, treatment with the second agent occurs before treatment with the composition of this invention. In another embodiment, treatment with the second agent occurs after treatment with the composition this invention. In yet a further embodiment, treatment with the second agent occurs concurrently or simultaneously with treatment with the compositions defined herein.

In another aspect, the method of the present invention involves inducing apoptosis in an epithelial-derived cancer cell by treating the cells with a composition of this invention. In still another aspect, the method of the present invention involves inducing apoptosis in a breast cancer cell by treating the cells with a composition of this invention. The following description further describes methods of treating other cancers, particularly cancers resistant to other apoptogens with the compositions described herein.

In still another aspect, the invention provides a method of determining sensitivity of cancer cells to apoptosis by contacting said cancer cells in culture with a suitable amount of a composition described herein and measuring the rate of apoptosis in said culture.

In another aspect, the invention provides a pharmaceutical kit for the treatment of cancer comprising at least one composition as defined above in a dosage unit. In one aspect, the kit contains cystine dimethyl ester, as well as optional components such as suitable pharmaceutically or diagnostically acceptable carriers, penetration enhancers or components for extending bioavailability and increasing its resistance to enzymatic degradation in vivo, fusion compounds, detectable reagents, physical delivery means and other similar items.

In a further aspect, the invention provides the use of a compound or composition described above in the preparation of a medicament for the treatment or prophylaxis of cancer in a mammalian subject.

Other aspects and advantages of the present invention are described further in the following detailed description of the preferred embodiments thereof.

BRIEF DESCRIPTION OF THE FIGURES

FIG. 2 is a table indicating the effect of various disulfide compounds and esters thereof on apoptosis of renal fibroblasts, as well as drawings of the structures therein. None of the structures other than cystine dimethylester caused significantly increased apoptosis in human proximal renal tubule epithelial cells.

DETAILED DESCRIPTION OF THE INVENTION

Figure 1:
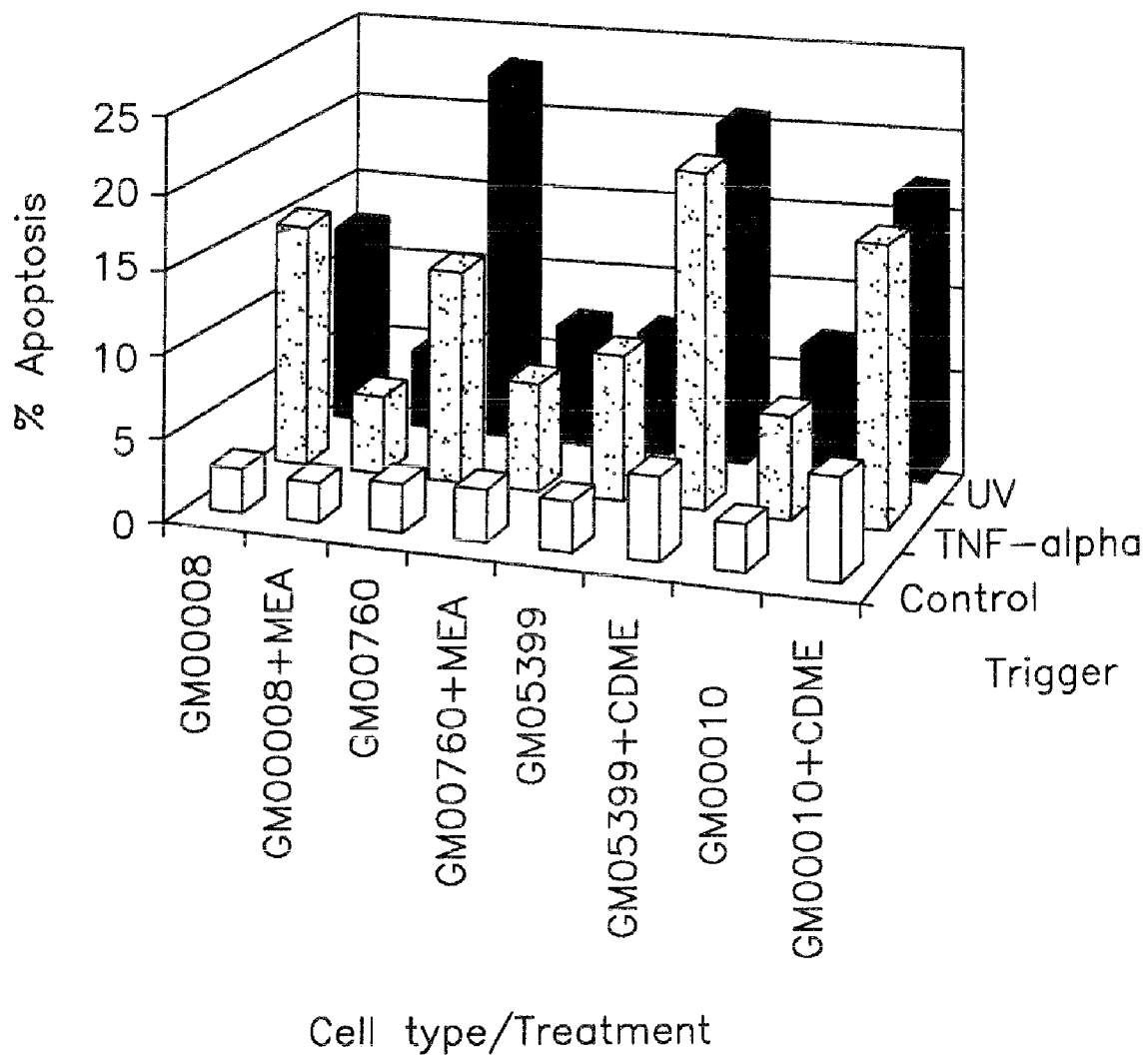
FIG. 1 is a bar graph showing the effect of MEA or cystine dimethylester (CDME) on apoptosis in semi-confluent nephropathic cystinotic or normal fibroblasts.

In response to the need of the art for additional apoptotic or apoptogenic compositions for the treatment of cancer, the present invention provides compositions useful for the treatment of cancer which includes a compound which is a di-alkyl ester based on cystine as defined by Formula (a) below or a compound which is di-alkyl peptidyl cystamine ester of Formula (b) below.

A. Compounds of the Invention

According to this invention, preferred compounds of the present invention are defined by the following formulae ("Formula (a)" and "Formula (b)" hereinafter collectively referred to as the "Formulae of the Invention"):

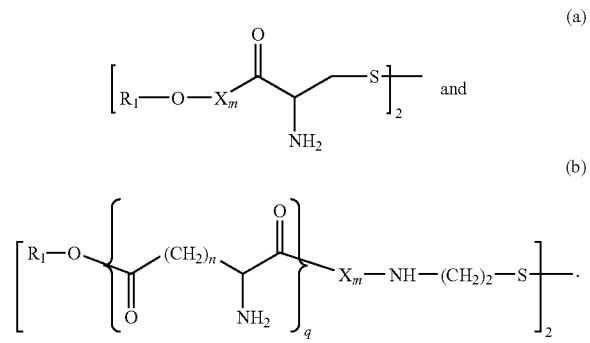

For compounds of both Formula (a) and Formula (b), $R_1$ is a substituted or unsubstituted alkyl of 1 to 10 carbon atoms. "Alkyl" is used herein to refer to both straight and branched-chain saturated aliphatic hydrocarbon groups having 1-10 carbon atoms. The term "substituted alkyl" refers to alkyls having one or more substituents including, without limitation, halogen, CN, OH, $NO_2$, amino, aryl, heterocyclic, alkoxy, aryloxy, alkylcarbonyl, alkyl, carboxy and arylthio, which groups can be otherwise substituted. These substituents can be attached to any carbons of the alkyl group, provided that the attachment constitutes a stable chemical moiety. In some preferred embodiments, $R_1$ is a straight chain alkyl of at least 1, 2, 3, 4, 5, 6, 7, 8, 9, or 10 carbons. In another embodiment, the $R_1$ is a methyl group. In another embodiment, the $R_1$ is a butyl group. Still other $R_1$ groups may be readily selected by one of skill in the art.

For compounds of both Formula (a) and Formula (b), X represents a naturally-occurring or non-naturally-occurring amino acid, and m is an integer of 0 to 20. "Naturally-occurring amino acid" is used herein to refer to the twenty amino acids that occur in nature in L form, which include alanine, cysteine, aspartate, glutamate, phenylalanine, glycine, histidine, isoleucine, lysine, leucine, methionine, aspargine, proline, glutamine, arginine, serine, threonine, valine, tryptophan, and tyrosine, or any derivative thereof produced through a naturally-occurring biological process or pathway.

"Non-naturally-occurring amino acid" is used herein to refer to an amino acid other than a naturally-occurring amino acid as defined above, which can be synthesized or "man-made", and including a derivative thereof, whether produced synthetically or via a biological process or pathway. Non-naturally occurring amino acids include, without limitation, D amino acids, amino acids containing unnaturally substituted side chains, e.g., methyl-Arg, cyclic amino acids, diamino acids, β-amino acids, homo amino acids. Non-naturally-occurring or unnatural amino acids may be characterized by novel backbone and side chain structures and are widely available from commercial reagent suppliers, such as Sigma-Aldrich (www.sigmaaldrich.com), www.Netchem.com and other sites. See also a broad literature on such structures including, without limitation, Han S and Viola R E, Protein Pept. Lett. 2004 11(2):104-14; Ishida et al, Biopolymers 2004 76(1):69-82; Sasaki et al, Biol. Pharm. Bull. 2004 27(2):244-7; Pascal R et al, Meth. Enzymol. 2003 369:182-94; Yoder N C and Kumar K, Chem. Soc. Rev. 2002 31(6):335-41; and Ager D J, Curr. Opin. Drug Discov. Devel. 2002 5(6):892-905, among others, which are incorporated herein by reference. This term does not encompass those derivatives which fall within the definition of a "naturally-occurring amino acid", as defined above.

Such non-naturally occurring amino acid(s) when employed in the compounds above are anticipated to make the compounds more resistant to degradation by mammalian enzymes in serum, saliva, stomach and intestines, and thus compounds that are composed of one or more such amino acids may confer upon the compound enhanced stability and bioavailability in vivo. A variety of methods for producing non-natural amino acids are known and may be selected by one of skill in the art.

For example, one class of non-naturally occurring amino acids are L amino acids that effect stereochemistry. Thus, in one embodiment of compounds of this invention, one or more of the amino acids in the peptide may be in L form, while others may be in D form. Another non-naturally occurring amino acid is an amino acid which is modified to contain a substitution on the alpha-carbon in the amino acid structure. For example the alpha-carbon may be substituted by a suitable hydrocarbon moiety, such as aminoisobutyrate. Still another class of non-naturally occurring amino acids is amino acids which are modified or mutated to extend their carbon chain length. For example, an amino acid with a single alpha-carbon chain, may be extended with at least one additional carbon, i.e., a beta-carbon, and so on. An additional modification to an amino acid is the insertion of a substituent on the nitrogen of the amino group. An example of this type of modification is an N-methyl amino acid. The addition of substituents on the alpha carbon or additional carbons or on the nitrogen of the amino acid molecule may occur in any of the amino acids of the formula above.

Among useful substituents for creating the non-naturally occurring amino acids are a straight chain, branched, cyclic or heterocyclic $C_{1-12}$ alkyl group, and straight chain, branched, cyclic, or heterocyclic $C_{1-12}$ alkanoyl group. The amino acid may be also modified by the insertion of modifying sugars, imide groups and the like. Other amino acids are substituted in the ortho or meta position by a substituent such as H, OH, $CH_3$, halogen, $OCH_3$, $NH_2$, CH or $NO_2$.

A non-exclusive list of modified or non-naturally occurring amino acids for inclusion in compounds fitting the formula above include amino acids modified by N-terminal acetylation, C-terminal amidation, formylation of the N-terminal methionine, gamma-carboxyglutamic acid hydroxylation of Asp, Asn, Pro or Lys residues in the compound, methylation of Lys or Arg, preferably; phosphorylation of Ser, Thr, Tyr, Asp or His in the compound, use of a pyrrolidone carboxylic acid, which is an N-terminal glutamate which has formed an internal cyclic lactam, sulfation of Tyr, generally. Still other modifications of non-naturally occurring amino acids include use of or substitution with the following moieties: a 2-aminoadipic acid group, a 3-aminoadipic acid group, beta-Ala or beta-aminopropionic acid group, 2-aminobutryic acid, 4-aminobutyric acid, piperidinic acid, 6-aminocaproic acid, 2-aminoheptanoic acid, 2-aminoisobutryic acid, 3-aminoisobutyric acid, 2-aminopimelic acid, 2, 4 diaminobutyric acid, desmosine, 2,2'-diaminopimelic acid, 2,3-diaminopropionic acid, N-ethylglycine, N-ethylglycine, N-ethyl asparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, 6-N-methyllysine, norvaline, norleucine, and ornithine.

Thus, in certain embodiments of compounds of this invention, the naturally-occurring or non-naturally occurring amino acid(s) represented by $X_m$ can be absent. In other embodiments $X_m$ can be at least 1, 2, 3, 4, 5, 6, 7, 8, 9, 10, 11, 12, 13, 14, 15, 16, 17, 18, 19 or 20 amino acid residues. In still other embodiments, $X_m$ ranges from 1 to 15. In still other embodiments, $X_m$ ranges from 1 to 10 amino acids. Still other embodiments of this formula (a) contain 1 to 5 amino acids at the $X_m$ position. Still other preferred compounds are formed when $X_m$ is a single amino acid. Such amino acids represented by $X_m$ may be in D or L rotational form.

In another embodiment, a compound of the invention is provided in which $X_m$ of Formula (a) has one of the following two structures:

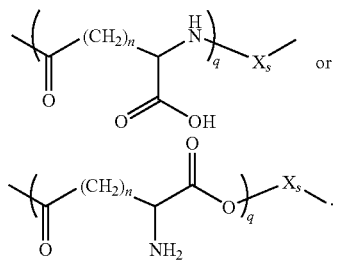

In these embodiments of $X_m$ for Formula (a) and for all embodiments of Formula (b), n is an integer of 1 or 2, and q is an integer of 0 or 1. X is defined as above, but s is an integer of 0 to 19.

Thus, in certain embodiment of compounds of Formula (a) or (b), wherein n is 1, the ester group on the lefthand end of the compound is formed by an Asp. In embodiments in which n is 2, the ester group is formed by a Glu residue. Depending upon the structure involved, the Asp or Glu can be a D-Asp, L-Asp, D-Glu or L-Glu.

In one such embodiment of Formula (a), wherein the Xs is absent, the compound formed is a di-alkyl aspartyl or dialkyl glutamyl ester derivative of cystine. In a particular embodiment of Formula (b), in which n is an integer of 1 or 2, and q is an integer of 0 or 1, with the $R_1$ and $X_m$ defined as above, a variety of dialkyl Asp or dialkyl Glu esters of cystamine are provided.

In a particular embodiment of this invention, a compound of Formula (a) is characterized by m being 0 and $R_1$ is a methyl group, resulting in the compound cystine dimethyl ester (CDME). In an embodiment of Formula (b), where q is 1 and m is 0, and where $R_1$ is a methyl group, a dimethyl asparatyl or dimethyl glutamyl ester derivative of cystamine is provided. In other embodiments, the invention provides for compounds wherein the variable elements are defined anywhere within the stated ranges.

B. Methods of Production

Compounds of the invention may be prepared conventionally by known chemical synthesis techniques. Compounds of the invention may also be purchased from a commercial vendor, e.g. the Sigma-Aldrich Co. Among such preferred techniques known to one of skill in the art are included the synthetic methods described by Merrifield, J. Amer. Chem. Soc., 1963 85:2149-2154; and in texts such as G. C. Barrett and D. T. Elmore, "Amino Acids and Peptides" October 1998; and "Peptides: Chemistry and Biology", eds. N. Sewald, H-D Jakubke, August 2002; and other conventional textbooks relating to the construction of synthetic compounds.

C. Pharmaceutical Compositions and Formulations

Pharmaceutical compositions of the present invention, in one embodiment, contain a compound of Formula (a) in a pharmaceutically acceptable carrier with other optional suitable pharmaceutically inert or inactive ingredients. In another embodiment, a pharmaceutical composition contains a compound of Formula (b) in a similar formulation. In another embodiment, pharmaceutical compositions of the present invention contain one or more compounds of the formulae described above or with one or more different therapeutically useful reagents. In one embodiment, a compound of Formula (a) and a compound of Formula (b) are present in a single composition. In another embodiment, a compound of Formula (a) and/or a compound of Formula (b) is combined with one or more chemotherapeutic apoptotic agents and/or biological apoptotic agents, radiological apoptotic agents, and/or other therapeutic agents as described below.

1. Salts

The compounds of the present invention when formulated in pharmaceutical compositions encompass tautomeric forms of the structures provided herein characterized by the bioactivity of the drawn structures. Further, the compounds of the present invention can be used in the form of pharmaceutically acceptable salts derived from pharmaceutically or physiologically acceptable acids, bases, alkali metals and alkaline earth metals.

Physiologically acceptable salts include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfamilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N-dibenzylethylenediamine, chloroprocaine, choline, diethanolamine, ethylenediamine, meglumine, and procaine, among others.

Physiologically acceptable alkali salts and alkaline earth metal salts include, without limitation, sodium, potassium, calcium and magnesium salts in the form of esters, and carbamates. Other conventional "pro-drug" forms can also be utilized which, when delivered in such form, convert to the active moiety in vivo.

These salts, as well as other compounds of the invention, are preferably in the form of esters for use as a "pro-drug" forms, which when administered in such form, converts to the active moiety in vivo. In another embodiment, the prodrugs are carbamates. See, e.g., B. Testa and J. Caldwell, "Prodrugs Revisited: The "Ad Hoc Approach as a Complement to Ligand Design", Medicinal Research Reviews, 16(3):223-241, ed., John Wiley & Sons (1996).

The compounds discussed herein also encompass "metabolites" which are products formed by processing the compounds of the invention by the cell or subject. Preferably, metabolites are formed in vivo.

2. Carriers

The pharmaceutical compositions of this invention include compounds of this invention formulated neat or with one or more pharmaceutical carriers for administration, the proportion of which is determined by the solubility and chemical nature of the compound, chosen route of administration and standard pharmacological practice. The pharmaceutical carrier(s) may be solid or liquid. Formulations may incorporate both solid and liquid carriers.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins, crystalline cellulose, binders such as hydroxypropylmethyl cellulose, coating agents such as hydroxypropylmethyl cellulose and terephthalate thereof, lubricants such as zinc stearate and aluminum stearate.

Liquid carriers are used in preparing solutions, suspensions, emulsions, syrups, elixers and pressurized compositions. The active ingredient can be dissolved or suspended in a pharmaceutically acceptable liquid carrier such as water, an organic solvent, a mixture of both or pharmaceutically acceptable oils or fats. Carriers include glycerol, propylene glycol, liquid polyethylene glycol, and the like. The liquid carrier can contain other suitable pharmaceutical additives such as solubilizers, emulsifiers, isotonic agents, sugars, sodium chloride, anti-oxidants, buffers, bacteriostats, preservatives, sweeteners, flavoring agents, suspending agents, thickening agents, surfactants, colors, viscosity regulators, stabilizers or osmo-regulators, tensio-active agents. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant, solubilizing and dispersing agents such as polyoxyethylene hardened castor oil, stabilizers, pH adjusters, and isotonicity-imparting agents, preservatives, anti-bacterial and anti-fungal agents, liposomes, mannose, glucose and balanced salt solutions, phosphate buffered saline, diethyl ether, isopropyl ether, halothane, or trifluorotrichloroethane.

3. Pharmaceutical Compositions Containing Multiple Compounds

Additionally, the compounds of the present invention may be formulated alone in a composition of the invention or may be formulated in combination with other compounds of the invention and other compounds known in the art of cancer treatment. Compounds of the present invention may also be used in combination with other therapeutic agents.

In certain embodiments, such other such agents include, but are not limited to chemotherapeutic apoptotic agents, such as anti-metabolites, DNA damaging, microtubule destabilizing, microtubule stabilizing, actin depolymerizing, growth inhibiting, topoisomerase inhibiting, HMG-CoA inhibiting, purine inhibiting, pyrimidine inhibiting, metalloproteinase inhibiting, CDK inhibiting, caspase inhibiting, proteaosome inhibiting, angiogenesis inhibiting, differentiation inducing and immunotherapeutic drugs, and compositions for promotion of TGF-β response and/or apoptosis. These agents include, but are not limited to, anthracycline antibiotics such as doxorubicin and mitoxantrone, estramustine, vinblastine, paclitaxel, etoposide, cyclophosphamide, cisplatin, carboplatin, adriamycin, 5-fluorouracil, camptothecin, actinomycin-D, mitomycin C, adriamycin, verapamil, podophyllotoxin, and the like (with or without the addition of steroid drugs); anti-androgens (such as flutamide, bicalutamide, nilutamide, megestrol acetate, adrenocorticotropic hormone secretion inhibitors, ketoconazole, estrogens, anti-estrogens and LHRH production suppressors), immunomodulatory agents (including cytokines, chemokines, interferons, interleukins), a non-progestin/non-estrogen apoptosis promoting agent selected from the group consisting of the retinoids (retinoic acid, N-(4-hydroxyphenyl) retinamide-O-glucuronide, N-(4-hydroxyphenyl) retinamide, O-glucuronide conjugates of retinoids, N-(4-hydroxyphenyl) retinamide and its glucuronide derivative, retinyl-β-glucuronide, the glucuronide conjugates of retinoic acid and retinol, tretinoin, etretinate, arotinoid, isotretinoin, retinyl acetate, acitretin, adapalene, and tazarotene), adamantyl or adamantyl group derivatives containing retinoid-related compounds (e.g., 6-[3-(1-adamantyl)-4-methoxyphenyl]-2-naphthoic acid, 2-[3-(1-adamantyl)-4-methoxyphenyl]-5-benzimidazole carboxylic acid, and 6-[3-(1-adamantyl)-4,5-methylenedioxyphenyl]-2-naphthoic acid; 2-methoxyestradiol), progestin, 1-O-acetylbritannilactone, 1,6-O,O-diacetylbritannilactone, a 2-nitroimidazole derivative (e.g. 1-(2,3-dihydroxy-1-(hydroxymethyl)-propoxymethyl)-2-nitroimidazole, 1-(4-hydroxy-2-butenyloxymethyl)-2-nitroimidazole and 1-(2,3-dihydroxypropoxymethyl)-2-nitroimidazole), benzamide riboside, synthetic glycoamines, TNF-a, anti-Fas antibody, thapsigargin, TGF-β (TGF-β-1, TGF-β-2 or TGF-β-3), non-progestin/non-estrogen TGF-β inducing agents, polyclonal antibodies, monoclonal antibodies, dietary flavanoids, anti-inflammatory drugs, monoterpenes, S-adenosyl-L-methionine, selenium, and vitamin D compound.

Other apoptotic agents include biological apoptotic agents such as a p53 protein or gene, *Mycobacterium phlei* (*M. Phlei*) DNA (M-DNA) & DNA complexed with *M. phlei* cell wall (MCC), extract of Melothria indica Lou, fetuin, Apogen P-1a, Apogen P-1b, Apogen P-1c, Apogen P-2, and Apogen L. Further apoptotic agents include radiological apoptotic agents such as radioisotopes and DNA damaging radiation such as X-rays, UV-light, gamma-rays and microwaves.

Other therapeutic agents not listed above, but which are beneficial in combination therapies of the invention, are contemplated as within the invention.

In one embodiment, compounds of the invention and/or other agents may be administered in a single composition. However, the present invention is not so limited. In other embodiments, compounds of the present invention may be administered in one or more separate formulations from other compounds of the invention, chemotherapeutic apoptotic agents, biological apoptotic agents, radiological apoptotic agents, or other agents as is desired.

Compounds and compositions of the present invention may be formulated for administration via sterile aqueous solution or dispersion, aqueous suspension, oil emulsion, water in oil emulsion, site-specific emulsion, long-residence emulsion, sticky-emulsion, microemulsion, nanoemulsion, liposomes, microparticles, microspheres, nanospheres, nanoparticles, minipumps, and with various natural or synthetic polymers that allow for sustained release. The compounds of the present invention may also be formulated into aerosols, tablets, pills, sterile powders, suppositories, lotions, creams, ointments, pastes, gels, hydrogels, sustained-delivery devices, or other formulations used in drug delivery.

The particular formulation or formulations used will vary according to the route(s) of administration desired. For example, injectable formulations can be prepared by combining the compositions with a liquid. The liquid can be selected from among water, glycerol, ethanol, glycols, such as propylene glycol and polyethylene glycol, oils, and mixtures thereof, and more preferably the liquid carrier is water. In one embodiment, the oil is vegetable oil. Optionally, the liquid carrier contains a suspending agent. In another embodiment, the liquid carrier is an isotonic medium and contains about 0.05% to about 5% suspending agent.

In one embodiment, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre-filled syringes or sachets containing liquids. The unit dosage form can be, for example, a capsule or tablet itself, or it can be an appropriate number of any such compositions in package form.

D. Pharmaceutical Kits

The present invention provides kits or packages of pharmaceutical formulations including the compounds or compositions described herein. The kits are also preferably organized to indicate a single oral formulation or combination of oral formulations to be taken at each desired time, preferably including oral tablets to be taken at each of the times specified, and more preferably one oral tablet will contain each of the combined periodic dosages indicated.

The kit can also include one or more chemotherapeutic apoptotic agents, biological apoptotic agents, or other therapeutic agents, such as one or more agent(s) selected from among those previously described. One of skill in the art would readily be able to formulate a suitable amount of the above-described agents for use in the kits of the invention. Kits containing radiological agents in combination with the compositions of the invention are also contemplated.

When the compounds or compositions described herein are to be delivered continuously, a package or kit can include the compound in each dosage unit (e.g. solution, lotion, tablet, pill, or other unit described above or utilized in drug delivery). When the compound is to be delivered with periodic discontinuation, a package or kit can include placebos during periods when the compound is not delivered. When varying concentrations of a composition, of components of a composition, or of relative ratios of compounds or agents within a composition over time is desired, a package or kit may contain a sequence of dosage units, so varying.

A number of packages or kits are known in the art for the use in dispensing pharmaceutical agents for oral use. Preferable, the package has indicators for each period, and more preferably is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another packaging means.

The kits of the present invention also will typically include a means for containing the vials in close confinement for commercial sale such as, e.g., injection or blow-molded plastic containers into which the desired vials are retained. Irrespective of the number or type of packages, the kits of the invention also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In one embodiment, a pharmaceutical kit of the invention including at least one composition containing a compound according to the Formulae of the Invention in a dosage unit. In another embodiment, a pharmaceutical kit of the invention contains at least one compound of Formula (a) and at least one compound of Formula (b) in a dosage unit. In another embodiment, a pharmaceutical kit of the invention contains cysteine dimethyl ester (CDME) in unit dosage form. In another embodiment, a pharmaceutical kit of the invention contains aspartyl-cystamine dimethyl ester in unit dosage form.

In still other embodiments, pharmaceutical kits of the invention also contain chemotherapeutic apoptotic agents, biological apoptotic agents, and/or other therapeutic agents as described above. In still other embodiments, pharmaceutical kits of the invention employ the above-described compositions along with radiological agents and treatments.

E. Methods of Treatment

The compositions of the present invention are useful in the treatment of cancers. Specific cancers to be treated with the compositions of the invention include estrogen negative breast cancer, estrogen positive breast cancer, prostate cancers (including androgen-independent prostate cancer), ovarian cancer, bladder cancer, brain cancer, head and neck cancer, kidney cancer, lung cancers such as small cell lung cancer and non-small cell lung cancer, myeloma, neuroblastoma/glioblastoma, pancreatic cancer, skin cancers, liver cancers, melanoma, colon cancer, cervical carcinoma, and leukemia, retinoblastoma, pancreatic islet carcinoma, or other epithelial-derived cancers.

In one embodiment, a method of treating or preventing the development of cancer in a mammalian subject comprising treating cancer cells of said subject with a composition of the invention is contemplated, either in vivo or ex vivo. The pharmaceutical compositions of the present invention may be administered to a subject via one or more routes to contact the cancer cells, as desired. For example, the compositions may be administered via oral, topical, systemic, enteral, parenteral (e.g., formulated for injection via the intravenous, intramuscular, subcutaneous, intracutaneous, or even intraperitoneal routes (e.g. by drip infusion)), subcutaneous, intra-portal, intra-prostatic, intra-muscular, intra-venous, intra-arterial, intra-dermal, intra-thecal, intra-lesional, intra-tumoral, intra-bladder, intra-vaginal, intra-ocular, intra-rectal, intra-pulmonary, intra-spinal, fransdermal, and subdermal routes. Further, the compositions may be delivered via placement within cavities of the body, regional perfusion at the site of a tumor or other desired location, nasal inhalation, pulmonary inhalation, impression into skin and electroporation. The route(s) of administration will vary according to the cell(s), tissue(s), organ(s), or system(s) to be treated.

In a further embodiment, the compounds are delivered transdermally or by sustained release through the use of a transdermal patch containing the composition and an optional carrier that is inert to the compound, is nontoxic to the skin, and allows for delivery of the compound for systemic absorption into the blood stream. Such a carrier can be a cream, ointment, paste, gel, or occlusive device. The creams and ointments can be viscous liquid or semisolid emulsions. Pastes include absorptive powders dispersed in petroleum or hydrophilic petroleum. Further, a variety of occlusive devices can be utilized to release the active reagents into the blood stream and include semi-permeable membranes covering a reservoir contain the active reagents, or a matrix containing the reactive reagents.

The use of sustained delivery devices can be desirable, in order to avoid the necessity for the patient to take medications on a daily basis. The term "sustained delivery" is used herein to refer to delaying the release of an active agent, i.e., a compound of the invention, until after placement in a delivery environment, followed by a sustained release of the agent at a later time. A number of sustained delivery devices are known in the art and include hydrogels (U.S. Pat. Nos. 5,266,325; 4,959,217; 5,292,515), osmotic pumps (U.S. Pat. Nos. 4,295,987 and 5,273,752 and European Patent No. 314,206, among others); hydrophobic membrane materials, such as ethylenemethacrylate (EMA) and ethylenevinylacetate (EVA); bioresorbable polymer systems (International Patent Publication No. WO 98/44964 and U.S. Pat. Nos. 5,756,127 and 5,854,388); and other bioresorbable implant devices composed of, for example, polyesters, polyanhydrides, or lactic acid/glycolic acid copolymers (U.S. Pat. No. 5,817,343). For use in such sustained delivery devices, the compounds of the invention can be formulated as described herein. See, U.S. Pat. Nos. 3,845,770; 3,916,899; 3,536,809; 3,598,123; and 4,008,719.

The methods of this invention involve administering such compositions in effective amounts to induce apoptosis in the cancer cells, while minimizing adverse impacts on non-cancer cells of the patient. Dosages of the compounds and compositions of the present invention vary with the particular compositions employed, the route of administration, the severity of the symptoms presented, the particular subject being treated, and the subjects other medications and treatment, as well as the subject's medical history. Precise dosages for oral, parenteral, nasal, or intrabronchial administration can be determined by the administering physician based on experience with the individual subject treated. An effective therapeutic dosage will contain a dosage sufficient to induce apoptosis of cancer cells. In one embodiment, the dosage of composition of the present invention is such that administration will increase a cell's intralysosomal cystine above 0.5 nmol/mg cell protein.

The amount of the compound of the invention present in each effective dose is selected with regard to consideration to the half-life of the compound, the identity and/or stage of the cancer, the patient's age, weight, sex, general physical condition and the like. The amount of active component or compound required to induce an effective apoptotic effect on cancer cells without significant adverse side effects varies depending upon the pharmaceutical composition employed and the optional presence of other components. Suitable dosages of compositions used to treat cancers as described herein can range from 1.0 µg to 500 mg compound(s)/kg patient body weight. In one embodiment, the dosage is at least 10 µg/kg. In another embodiment, the dosage is at least 100 µg/kg. In another embodiment, the dosage is at least 500 µg/kg. In another embodiment, the dosage is at least 1 mg/kg. In another embodiment, the dosage is at least 10 mg/kg. In another embodiment, the dosage is at least 50 mg/kg. In another embodiment, the dosage is at least 100 mg/kg. In another embodiment, the dosage is at least 250 mg/kg. In another embodiment, the dosage is at least 400 mg/kg. In another embodiment, the dosage is at least 500 mg/kg. In another embodiment, each dose will contain between about 5 µg peptide/kg patient body weight to about 10 mg/kg. Generally, a useful therapeutic dosage is between 1 to 5 mg peptide/kg body weight. Another embodiment of a useful dosage may be about 500 µg/kg of peptide. Other dosage ranges may also be contemplated by one of skill in the art. For example, dosages of the peptides of this invention may be similar to the dosages discussed for other cancer therapeutics.

Initial doses of a composition of this invention may be optionally followed by repeated administration for a duration selected by the attending physician. Dosage frequency may also depend upon the factors identified above, and may range from 1 to 6 doses per day for a duration of about 3 days to a maximum of no more than about 1 week. The compositions of this invention may also be administered as a continuous infusion for about 3-5 days, the specific dosage of the infusion depending upon the half-life of the compound. The compounds of this invention may also be incorporated into chemotherapy protocols, involving repetitive cycles of dosing. Selection of the appropriate dosing method would be made by the attending physician.

In another embodiment of this invention, the method of treating or preventing the development of cancer in a mammalian subject involves exposing the subject to one or multiple (e.g. 2, 3, 4, or more) chemotherapeutic apoptotic agents, biological apoptotic agents, radiological apoptotic agents, or other therapeutic agents described herein. Such combination treatment may occur by administering compositions containing multiple active ingredients, as described above. However, this invention also encompasses a method of administration of anti-cancer agents or therapies in conjunction with a composition containing a compound of formulae (a) or (b) as described above. In one embodiment of such a method, the active ingredients are administered to the patient by one or more selected routes of administration sequentially. In one embodiment, a chemotherapeutic agent is administered before treatment with a composition of the invention. In another embodiment, a chemotherapeutic agent is administered after treatment with a composition of the invention. In still another embodiment, a chemotherapeutic agent is administered during treatment with a composition of the invention. In one embodiment, a chemotherapeutic agent is administered before treatment with a composition of the invention. In another embodiment, a chemotherapeutic agent is administered after treatment with a composition of the invention. In still another embodiment, a chemotherapeutic or biological apoptotic agent is administered before, during or after treatment with a composition of the invention.

In still another embodiment, the patient is exposed to radiological treatment administered before, during or after treatment with a composition of the invention. Where a radiological agent is desired in combination with one or more of the compounds or compositions of the present invention, dosage may be determined by an administering physician according to standard regimens taking into account other factors including other treatments applied in combination. For example, the appropriate regimen of radiation dosage ranges for X-rays ranges from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by cells.

In specific embodiments of this invention, a method of treating or preventing the development of cancer in a mammalian subject involves treating cancer cells of a patient with cystine dimethyl ester (CDME) as the composition in question. As discussed in the following examples, CDME is employed as the prototypic compound of formula (a) and induces accumulation of cystine in the lysosomes of cells, resulting in apoptosis. CDME is also found to enhance the apoptotic function of other apoptogens.

In another embodiment, a method of treating or preventing the development of cancer in a mammalian subject involves treating cancer cells of said subject with aspartyl-cystamine dimethyl ester, or other compounds described herein in the manner exemplified with CDME.

F. Use of the Compounds of the Invention in Screening Cancer Cells for Sensitivity An additional embodiment of this invention is a method of determining sensitivity of cancer cells to apoptosis, and specifically determining the susceptibility of a cancer patient to treatment with a composition or treatment regimen of this invention. According to this method, a sample of a patient's cancer cells in culture are contacted with a suitable amount of a composition of the invention and the rate of apoptosis in the culture is measured. The screening described may be conducted using techniques commonly known and used in the art. Examples of such assays are described herein in Examples.

For example, a tumor cell sample may be obtained from a patient, and maintained in a suitable medium, e.g., RPMI 1640+10% FCS. Suitable (e.g., 100 μL) aliquots of cell suspension (e.g., $5 \times 10^5$ cells/mL) are then cultured in flat-bottomed 96 well plates in the presence of different concentrations and compounds of formulae (a) and (b). After a suitable time of incubation (e.g., 1-72 hours) at room temperature or higher (e.g., 23-37° C.) in humidified air containing 5% $CO_2$, viable cell number can be determined by a suitable assay, such as an MTT assay. An MMT assay is conducted as follows: 10 μL of 3-[4,5-dimethylthiazol-2-yl]-2,5-diphenyl tetrazolium bromide (MTT) (5 mg/mL concentration) (Sigma) is added to each well and incubated further for 6 h. Formazan crystals that are formed during incubation were dissolved in 100 μL of acidified isopropanol. The optical density at 550 nm (which is linearly related to the number of viable cells) was measured using a plate spectrophotometer. Growth characteristics of the cancer cells are determined for cells by Trypan Blue exclusion.

Diminished cell viability in a concentration-dependant fashion in comparison to a negative control and optionally a positive control provides evidence that the selected compound of this invention induced apoptosis in the cancer cells. Other assays, such as the apoptosis assays described in Example 1 below may also be employed to determine sensitivity of a particular cancer cell to compounds of this invention. One of skill in the art may readily select a suitable assay for this determination.

EXAMPLES

The following examples illustrate various aspects of this invention. These examples do not limit the scope of this invention which is defined by the appended claims. One skilled in the art will appreciate that although specific reagents and conditions are outlined in the following examples, modifications can be made which are intended to be encompassed by the spirit and scope of the invention.

Example 1

Methods and Materials

A Cell Cultures

Normal and cystinotic fibroblasts were purchased from the Coriell Mutant Cell Repository, and cultured in Coon modification of Ham $F_{12}$ medium, supplemented with 10% fetal calf serum (FCS). Renal proximal tubule epithelial (RPTE; Biowhittaker Corp.) were cultured in renal epithelial basal medium supplemented with one Singlequots™ kit (Biowhittaker) per 500 mL to make renal epithelial growth media (REGM, Biowhittaker). Fibroblasts and RPTE were maintained in a 5% carbon dioxide, 95% air, humidified incubator at 37° C. (Thoene J. G. et al, 1976 *J. Clin. Invest*, 58:180-189).

The cell lines studied, their genotypes, and nominal cystine content are listed in Table 1 below. The cystine content was measured by a cystine binding protein assay described below. The mutations in cell lines GM00008, GM00760, and GM00046 cause typically severe nephropathic cystinosis with ESRD by 10 years of age. The cystine content shown in the cystinotic lines in Table 1 varies between 0.8 and 15.7 nmol/mg protein, which is that typically seen in cultured cystinotic fibroblasts.

TABLE 1

Genotype and cystine content of cell lines

| Cell Line | Phenotype | Genotype | Cystine Content (nmol/mg protein) |
|---|---|---|---|
| GM00008 | Nephropathic | 46XX. 65-kb del | 7.5 |
| GM00760 | Nephropathic | 46XY, 753 G3A, premature stop | 0.78 |
| GM00046 | Nephropathic | 46XY, 5-bp del. Frameshift | 1.51 |
| GM08761 | Ocular | 46XX, not determined | 6.29 |
| GM00379 | Intermediate | IVSl1__2 T3C | 15.7 |
| GM00010 | Normal | 46XY, apparently normal | 0.01 |
| GM05399 | Normal | 46XY, apparently normal | 0.01 |
| RPTE | Normal | 46XY, apparently normal | 0.6 |

B. Induction of Apoptosis

Induction of apoptosis and assays for its detection were performed using commercially available reagents. Normal and cystinotic fibroblasts were matched for passage number (±3) and cell density, and then exposed to an apoptotic trigger. One apoptotic trigger used was TNF-a (30 ng/mL) with actinomycin D (2.5 µg/mL) for 16 hours. Another trigger was anti-Fas antibody (500 ng/mL) with actinomycin D (2.5 µg/mL) for 16 hours. A third trigger to induce apoptosis in the cells was Ultraviolet B light (60 mJ). See, e.g., previously described protocols of Aggarwal B B, 1992 *Immunol. Ser.*, 56:61-78; Higuchi M. et al, 1995 *J. Immunol. Meth.*, 178:173-181; Itoh N, et al, 1991 *Cell*, 66:233-243; Itoh N. et al, 1993 *J. Biol. Chem.*, 268:10932-10937. Serum withdrawal was also used as a apoptotic stimulus (Lieberthal W, et al, 1998 *Am. J. Physiol.* 275:F691-F702; Verzola D. et al, 2001 *Exp Nephrol.*, 9:366-371; Iglesias J. et al, 1999 *Am. J. Physiol.* 277:F711-F712; Kulkarni G V, et al, 1994 *J. Cell Sci.*, 107: 1169-1179), in which case the cells were incubated in $F_{12}$ medium without serum for 24 hours and then analyzed for apoptosis.

After exposure, the cells were maintained in Coon modification of Ham $F_{12}$ medium for 16 hours before analysis.

C. Apoptosis Assays

The cells were then assayed for apoptosis using three commercially available apoptosis assays.

1. The CaspACE Assay

CaspACE (Promega) is an FITC-conjugated cell-permeable form of the pan-caspase inhibitor zVAD-Fmk, which binds to activated caspase(s). Cells were incubated in FITC-VAD-Fmk-containing medium (10 µM for 30 minutes at 37° C.), washed, and then fixed in 10% buffered formalin (30 minutes at room temperature) before analysis. The cells were visually enumerated by fluorescence microscopy, scoring a minimum of five fields (250 to 300 cells) for fluorescence in triplicate followed by counting all cells in the same field by light microscopy, with a minimum of 750 cells scored per condition. The apoptosis rate is the total number of cells that fluoresce divided by the total cells in the field.

2. TUNEL Assay

The TUNEL assay employs terminal deoxynucleotidyl transferase (TdT) to label the ends of double stranded DNA breaks, which occur in apoptotic cells, with FITC-conjugated dUTP. Cells were fixed in 4% buffered formalin, washed, incubated in permeabilization solution (0.1% Triton X-100 in 0.1% Na Citrate) for 2 minutes on ice and then stained with 25 µL of TdT/45 µL of labeled dNTP mix for 40 minutes at 37° C. The cells were visually enumerated by fluorescence microscopy, scoring a minimum of five fields (250 to 300 cells) for fluorescence in triplicate followed by counting all cells in the same field by light microscopy, with a minimum of 750 cells scored per condition. The apoptosis rate is the total number of cells that fluoresce divided by the total cells in the field.

3. The Annexin V Assay

Annexin V-propidium iodide (PI) staining was performed as described by the manufacturer (Annexin V Fluos kit directions, Roche Laboratories) one time after TNF-a stimulation.

D. Cystine Binding Protein Assay

Intracellular lysosomal free cystine was determined using a cystine binding protein (CBP) assay (Oshima et al, 1974 *J. Biol. Chem.*, 249:6033-6039). CBP was procured from Riverside Scientific. The assay has a sensitivity of 0.1 µM. Total cell protein was determined by a modification of the Lowry method (Lowry O. et al 1951 *J. Biol. Chem.*, 193:265-275).

Figure 3:
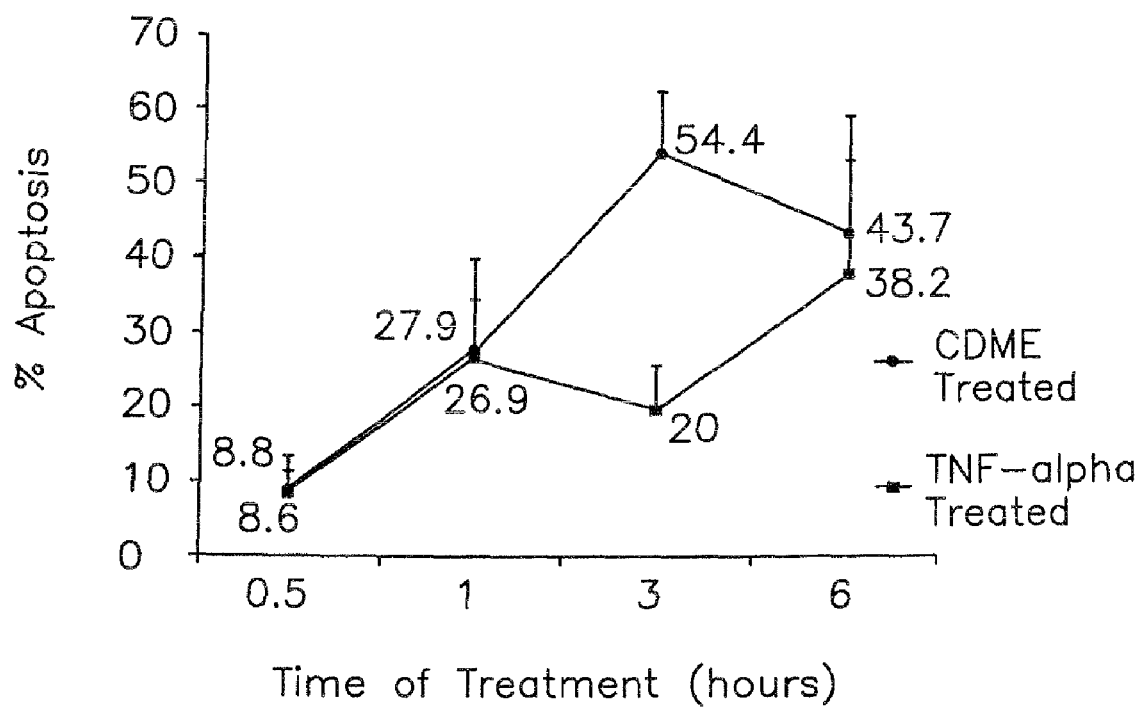
FIG. 3 is a graph showing the effect of CDME on apoptosis in renal proximal tubule epithelial (RPTE) cells. Semi-confluent RPTE cells were treated with either 0.25 mM CDME or TNF-a, harvested at 0.5, 1, 3, and 6 hours, stained with TUNEL, and enumerated by fluorescence microscopy. Each experiment was done in triplicate. The control (time 0) cystine content was 0.6 nmol/mg protein. After 1 hour incubation, the cystine content was 2.2 nmol/mg protein.

Statistical analyses were performed using paired t test for means with SSPS for Windows. Results are mean+/−1.0 SD (FIG. 3).

E. Immunohistochemistry of Normal and Cystinotic Fibroblasts

Cells were stained by Lysotracker® Red stain (Molecular Probes) for 5 minutes at room temperature, washed twice in PBS, and then fixed in 4% formalin for 1 hour. Slides were immersed in blocking buffer (PBS, pH 7.2, 0.5% Carnation® dry milk, 0.1% Triton® X-100 reagent) for 20 minutes at room temperature, washed twice in PBS, and then incubated with primary antibody (anti-cathepsin B, Santa Cruz Biotechnologies) diluted 1:100 for 2 hours at room temperature, followed by incubation with secondary antibody (FITC-conjugated rabbit anti-goat, Santa Cruz Biotechnologies), at 4° C. overnight. Slides were washed twice with PBS and then sealed with cover slips and viewed using a Leica® DMRX deconvoluting microscope.

Example 2

Lysosomal Cystine Storage Augments Apoptosis in Cultured Human Fibroblasts and Renal Tubular Epithelial Cells A. Apoptosis Induced in Untreated Cells Apoptosis was induced in three nephropathic cystinotic, two normal, one intermediate cystinotic, and one ocular cystinotic fibroblast lines by three separate inducers. In one experiment, cells were treated with apoptosis inducers as indicated above. Apoptosis in these lines was assessed by CaspACE assay and analyzed by fluorescence microscopy. A minimum of 250 cells was scored per condition, in triplicate. Thus at least 750 cells were scored precondition. T-statistics: $P<0.001$ for average nephropathic versus average normal. $P<0.05$ for ocular versus nephropathic. $P>0.05$ for ocular versus normal, intermediate versus nephropathic, and intermediate versus normal.

The results of this experiment are shown in Table 2. The cystinotic cells on average displayed about 2 to 3 times the apoptotic rate for the three apoptotic triggers compared with the normal cell lines. The cystinotic variant lines did not show increased apoptosis under these conditions. The differences were statistically significant at $P=0.05$ between the averages for cystinotic and normal lines and between nephropathic and ocular cystinotic lines. There was no significant difference in the rate of apoptosis between intermediate and nephropathic lines, ocular cells and normal cells, or intermediate versus normal cells.

TABLE 2

The apoptosis rate in cystinotic nephropathic, variant, and normal fibroblasts

| | | % Apoptosis | | | |
| | | Apoptotic Agents | | | |
| Cell Line | Phenotype | TNF-a | Anti-Fas antibody | Ultraviolet radiation | CONTROL |
| GM00008 | Nephropathic | 14.9 | 17.7 | 12.8 | 2.2 |
| GM00760 | Nephropathic | 13.5 | 14.4 | 26.3 | 3.1 |
| GM00046 | Nephropathic | 16.1 | 22.3 | 13.1 | 2.2 |
| AVG (of 3 nephropathic) | | 14.8 | 18.1 | 17.4 | 2.5 |
| GM08761 | Ocular | 8.2 | 5.9 | 6.4 | 2.3 |
| GM00379 | Intermediate | 11.4 | 7.7 | 8.4 | 3.1 |

TABLE 2-continued

The apoptosis rate in cystinotic nephropathic, variant, and normal fibroblasts

| | | % Apoptosis | | | |
|---|---|---|---|---|---|
| | | Apoptotic Agents | | | |
| Cell Line | Phenotype | TNF-a | Anti-Fas antibody | Ultraviolet radiation | CONTROL |
| GM00010 | Normal | 9.2 | 6.5 | 7.0 | 2.8 |
| GM05399 | Normal | 6.3 | 4.9 | 7.2 | 1.9 |
| AVG (of 2 normal) | | 7.8 | 5.2 | 7.1 | 2.4 |

In another experiment, cells were treated with apoptosis inducers as indicated, stained with TUNEL reagent, and analyzed by florescence microscopy. A minimum of 250 cells were scored per conditions in triplicate. P>0.05 for between all pairs of nephropathic cystinotic cells and the intermediate cell line, and both normal lines except for those indicated by asterisk in Table 3 below, which were not significantly different from either normal line. P>0.05 for ocular versus normal and intermediate; P=0.01 for ocular versus nephropathic. As reported in Table 3, line GM00008 did not differ significantly from the normal lines' response after anti-Fas or UV exposure, nor did line GM00046 after TNF-a exposure. Again, the variant lines did not show augmented apoptosis compared with the normal fibroblast lines.

TABLE 3

The apoptosis rate in normal and cystinotic fibroblasts

| | | % Apoptosis | | | |
|---|---|---|---|---|---|
| | | Apoptotic Agents | | | |
| Cell Line | Phenotype | TNF-a | Anti-Fas antibody | Ultraviolet radiation | CONTROL |
| GM00008 | Nephropathic | 17.1 | 12.3* | 13.7* | 3.1 |
| GM00760 | Nephropathic | 19.3 | 17.7 | 21.6 | 2.4 |
| GM00046 | Nephropathic | 15.3* | 15.9 | 19.2 | 2.6 |
| AVG (of 3 nephropathic) | | 17.2 | 15.3 | 18.2 | 2.7 |
| GM08761 | Ocular | 5.5 | 7.1 | 6.8 | 3.4 |
| GM00379 | Intermediate | 8.2 | 8.5 | 8.5 | 2.8 |
| GM00010 | Normal | 12.8 | 9.6 | 11.9 | 2.4 |
| GM05399 | Normal | 11.4 | 10.5 | 7.6 | 2.4 |
| AVG (of 2 normal) | | 12.1 | 10.1 | 9.8 | 2.4 |

B. Apoptosis Induced in Lysosomal Loaded Cells

Normal fibroblast lysosomes were loaded with cystine by the addition of 0.5 mM cystine dimethylester (CDME, Sigma) to normal culture medium for 1 hour before treatment (Pisoni, R L, et al, 1992 *Somat. Cell. Mol. Genet.*, 18:1-6). The cells were treated with apoptotic triggers, leaving CDME in the medium to prevent lysosomal cystine loss, and then analyzed for apoptosis.

Lysosomal cystine loading of RPTE cells was accomplished by exposure to 0.1 mM or 0.25 CDME in normal REGM for 1 hour before treatment with or without apoptotic triggers.

Modulation of the apoptotic response was obtained by altering the lysosomal cystine content of normal or nephropathic cystinotic fibroblasts. Nephropathic cystinotic fibroblasts (passage 7-13) were subjected to lysosomal cystine depletion by treating the cells with 1 mM cystamine-HCl (MEA; Sigma) (Thoene et al, 1976 *J. Clin. Invest.* 58:180-189) in Ham $F_{12}$ medium lacking cystine (Life Technologies), with 10% FCS for 1 hour before exposure to apoptotic triggers, depleting them to a normal lysosomal cystine content (0.01 to 0.13 nmol of cystine per mg of protein). This pretreatment in cystine-free medium inhibits cystine re-accumulation.

The lysosomal cystine content of normal fibroblasts was also altered as follows. Normal fibroblasts also at passage 7-13 were pretreated with 0.5 mM CDME for 1 hour, increasing the cystine content of their lysosomes to the cystinotic range (0.47 to 1.95 nmol of cystine per mg of protein).

Both normal cells (2 cell lines) and nephropathic cells (2 cell lines) were then treated with apoptotic stimuli, i.e., ultraviolet radiation (UV), TNF-α or a control and incubated for 16 hours while in cystine-free or CDME-containing medium. Apoptosis was assayed by CapsACE assay, as described above.

The results are reported in FIG. 1, which shows the apoptosis rates induced by exposure to TNF-a or UV radiation, before and after correction of the cystine content of nephropathic fibroblasts to normal levels with MEA, and before and after pre-incubation with CDME. The mean rate of apoptosis for the cystinotic cells before cystine depletion was 15.6+/−2.7%; after cystine depletion by exposure to MEA, it fell to 6.1+/−2.8%. This difference is significant at P<0.001. The average control apoptotic rate for the normal fibroblast lines was 7.2+/−1.3%, which rose to 18.7+/−5.4% after exposure to CDME (P<0.001). The effect holds whether induction was by TNF-a or UV light.

Fluorescence micrographs (not shown) also displayed this effect of lysosomal cystine in normal and nephropathic cystinotic fibroblasts after exposure of non-treated and CDME-pretreated normal and nephropathic cystinotic fibroblasts to UV light (60 mJ). The high rate of apoptosis in cystinotic fibroblasts with initial cystine content of 4.0 nmol/mg protein fell after treatment with cystamine, which lowered the cystine content to <0.1 nmol/mg protein. The normal rate of apoptosis in normal fibroblasts (cystine content <0.1 nmol/mg protein) increases to a rate similar to that seen in cystinotic fibroblasts after pre-exposure of the cells to CDME, which increased the cystine content to 1.95 nmol/mg protein.

Phase micrographs (not shown) were also obtained of normal fibroblasts after TNF-α exposure alone, in normal fibroblasts in CDME, and in nephropathic fibroblasts after TNF-α exposure alone. Typical apoptotic morphology was observed, i.e., typical blebs in the plasma membrane are seen after treatment with TNF-a in both normal and cystinotic cell lines and the modulating effects of MEA and CDME was seen. More apoptotic cells were seen in cystinotic than normal cells. Enhanced apoptosis is seen in normal cells to which CDME is added. More normal morphology is seen in nephropathic cystinotic cells after MEA treatment.

In another experiment, the cystine content was decreased in cystinotic cells from 2.3 to 0.5 nmols cystine/$10^6$ cells by pretreatment with MEA before incubation in cystine-free and serum-free Ham $F_{12}$ medium. The cystine content in normal cells was increased from 0.4 to 1.3 nmols cystine/$10^6$ cells by treatment with CDME before incubation in serum-free Coon F12. Cells were stained with CaspACE and analyzed. As demonstrated in Table 4, serum withdrawal in cultured fibroblasts caused less apoptosis above baseline than the other stimuli employed; however, increasing lysosomal cystine, either naturally due to defective CTNS function or artificially due to CDME loading, again resulted in an increased apoptotic rate. P=0.068 for 008 serum withdrawal versus 05399 serum withdrawal; P=0.172 for 008 serum withdrawal versus 008 serum withdrawal plus MEA; and P=0.006 for 05399 serum withdrawal versus 05399 serum withdrawal plus CDME.

TABLE 4

Apoptosis in normal and nephropathic cystinotic fibroblasts exposed to serum withdrawal

| | % Apoptosis | |
|---|---|---|
| Condition | GM00008 cells | GM005399 cells |
| Untreated controls | 2.8 | 3.1 |
| Serum withdrawal | 8.7 | 6.1 |
| Serum withdrawal and MEA | 7.2 | — |
| Serum withdrawal and CDME | — | 37.3 |

To substantiate that lysosomes are perneabilized by TNF-a (Guicciardi M, 2000J. Clin. Invest., 106:1127-1137) under these conditions, cathepsin B (a lysosomal cysteine protease) was localized by immunohistochemistry in normal and nephropathic cystinotic cells before and after induction of apoptosis. Fibroblasts were maintained under normal culture conditions, exposed to TNF-a, loaded with Lysotracker® red reagent, fixed, and stained for cathepsin B using an anti-cathepsin B antibody. Photographs were made via a deconvoluting microscope.

Lysosomes were identified with Lysotracker red dye. Loss of colocalization of cathepsin B in normal and nephropathic cystinotic fibroblasts after TNF-a exposure was observed. In both normal and cystinotic fibroblasts before TNF-a treatment, cathepsin B displayed a punctuate pattern that is closely associated with the red lysosomal dye. Induction of apoptosis by TNF-a caused a translocation of cathepsin B from a lysosomal location to a diffuse cytosolic location, with loss of co-localization of color. Loss of granularity and decreased colocalization was observed in normal fibroblasts control cells versus normal fibroblasts treated with TNF-a, and in cystinotic control cells versus cystinotic cells treated with TNF-a.

Example 3

Effects of Various Compounds on Rate of Apoptosis

Cultured human renal proximal tubule epithelial cells were incubated with various apoptotic compounds at a concentration of 0.5 mM for 16 hours. The structures of the treatment compounds are shown in FIG. 2. Following incubation, cells were stained with CaspASE. Fluorescence-activated cell sorting (Beckman Coulter Epics Elite) was used to determine the percentage of cells undergoing apoptosis from each treatment group.

RPTE cells display marked apoptosis only after CDME exposure (39.7%). The concentration employed in fibroblasts (0.5 mM) was toxic to these cells and was decreased to 0.1 or 0.25 mM for the RPTE experiments. The rate of apoptosis produced by 0.25 mM CDME alone was equal to that induced by exposure to TNF-a alone. The time course was accelerated, with these cells attaining a maximum rate of apoptosis within 6 hours, (as opposed to 17 hours in fibroblasts) followed by lysis and release from the culture dish (see FIG. 3). The RPTE cystine content after exposure to 0.25 mM CDME for 1 hour was 1.99 nmol/mg protein. Fluorescence micrographs (not shown) at each time point showed the effect of CDME on apoptosis in RPTE cells at 0.5, 1, 3, and 6 hours.

Exposure of RPTE cells to TNF-a after cystine loading by exposure to 0.1 mM CDME and analysis by Annexin V and Propidium iodide staining yielded 4.3% Annexiv V positive cells and zero PI positive cells at 1 h after exposure, 9.5% and 1.7% at 3 hours and 25.3% and 9.1% at 6 hours. The proportion of necrotic RPTE cells increased with duration of exposure to CDME, but remained substantially less than the number of those that are apoptotic.

Example 4

Effect of CDME on Apoptosis in Human Breast Cancer Cell Lines

The apoptotic effect of CDME was compared to that of tamoxifen using the CaspACE™ assay system (Promega) and conventional flow cytometry techniques.

All cell lines were obtained from the American Type Culture Collection, P.O. Box 1549, Manassas, Va., 20108 unless otherwise indicated. The cell lines studied were estrogen receptor-negative breast cancer cell lines MDA-MB-231 (ATCC Accession No. HTB-26) and MDA-MB-468 (ATCC Accession No. HTB-132) and estrogen receptor-positive breast cancer cell lines, MCF-7 (ATCC Accession No. HTB-22) and T-47D (ATCC Accession No. HTB-133).

All cell lines were grown on the bottom of 12-well flasks in Gibco RPMI-1640, until they reached the confluency of about 50%. After that, the medium was exchanged with DMEM (Sigma, D-5030), supplemented with 10% charcoal-treated FBS.

After four days (at confluency of about 75%), cells were treated by exposure to either CDME (500 µM) or tamoxifen (100 µM) or neither for 16 hours at 37° C. CaspACE™ assay analysis of the treated and control cells was performed as described in Example 2 and measured via flow cytometry. Note that the dosage of tamoxifen was a maximum positive control dose, higher than that normally administered for chemotherapy.

Figure 4:
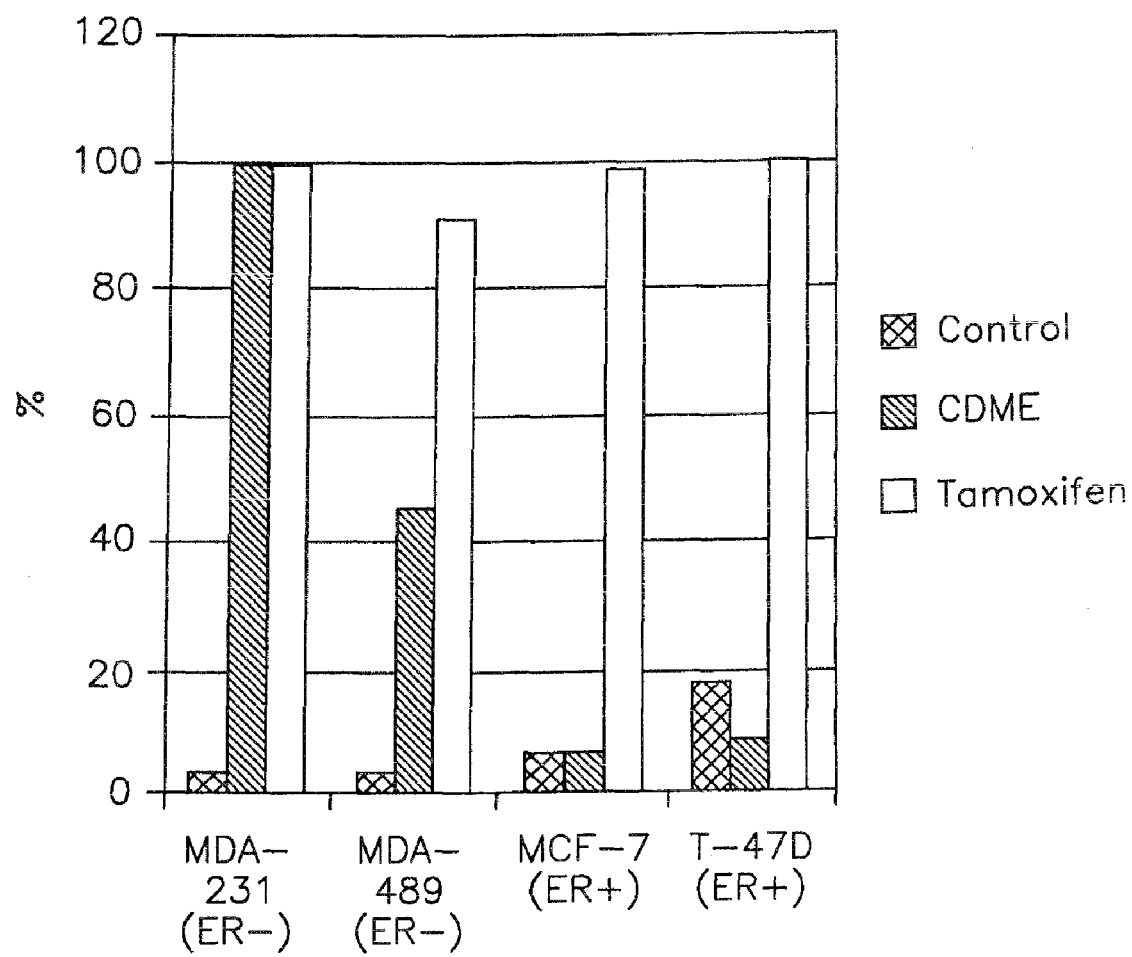
FIG. 4 is a bar graph showing percent of apoptotic cells following treatment of breast cancer cell lines MDA-231, MDA-489, MCF-7 and T74D with control, CDME and a known apoptotic agent, tamoxifen.

The above-described experimental procedure yielded the results shown below in Table 5, displayed graphically in FIG. 4. The results demonstrate CDME's effectiveness in inducing significant apoptosis at varying degrees in two estrogen receptor-negative breast cancer cell lines. The effect on ER+ breast cancer cells was no better than the negative control.

TABLE 5

CDME Induction of Apoptosis*

| Cell Line | Control | CDME (500 µM) | Tamoxifen (100 µM) | p-value (CONTROL vs. CDME) |
|---|---|---|---|---|
| MDA-MB-231 (ER−) | 3.18 ± 0.91 | 99.32 ± 0.22 | 98.92 ± 0.99 | <0.001 |
| MDA-MB-468 (ER−) | 2.54 ± 0.50 | 44.88 ± 13.52 | 90.37 ± 1.70 | <0.001 |

TABLE 5-continued

CDME Induction of Apoptosis*

| Cell Line | Control | CDME (500 μM) | Tamoxifen (100 μM) | p-value (CONTROL vs. CDME) |
|---|---|---|---|---|
| MCF-7 (ER+) | 6.29 ± 1.42 | 6.16 ± 1.80 | 98.47 ± 0.53 | 0.91 |
| T-47D (ER+) | 17.08 ± 3.77 | 7.78 ± 4.19 | 99.91 ± 0.08 | 0.02 |

*Values in Table 5 represent percent of apoptotic cells (±S.D.) with 10,000 cells/measurement. Mean values were compared using the t-test (sig. level 0.05)

Example 5

Toxicity Studies of CDME in Mice

CDME was evaluated in mice for cystine generation in response to varying doses as follows: A stock solution of CDME in PBS was prepared having a concentrations of 1.8 g CDME/500 μL PBS. The stock solution was diluted to generate solutions for administration. 500 μL of diluted solutions were injected intraperitoneally into black mice (body mass ~0.03 kg). All injections were performed in duplicate. The CDME solutions prepared and effective dosages per kg of mouse body weight for 500 μL injection are provided in Table 6.

TABLE 6

CDME Solutions

| Concentration of Final Solution | Effective Dosage |
|---|---|
| 300 mg CDME/500 μL PBS | 10,000 mg CDME/kg body mass |
| 150 mg CDME/500 μL PBS | 5,000 mg CDME/kg body mass |
| 15 mg CDME/500 μL PBS | 500 mg CDME/kg body mass |
| 1.5 mg CDME/500 μL PBS | 50 mg CDME/kg body mass |
| 0.3 mg CDME/500 μL PBS | 10 mg CDME/kg body mass |
| 0.03 mg CDME/500 μL PBS | 1 mg CDME/kg body mass |
| 500 μL PBS | 0 mg CDME/kg body mass |

Following administration of the solutions of Table 6, the endogenous cystine concentrations in two organs (kidney and liver) were examined for the 6 mice, i.e., the CDME-injected mice as well as black, heterozygous, and wild-type control mice. The analysis was performed using the cystine binding protein CBP assay of Example 1 and the Bicinchoninic Acid BCA assay (Pierce Biotechnology) for total protein concentration.

Mice given effective dosages of 5,000 mg CDME/kg body mass or higher died. The resulting data, presented below in Table 7, demonstrated elevated cystine levels in response to increased concentration of CDME in the injected solutions. The CDME-injected mice contained close to 100-fold increases in intralysosomal cystine. These results demonstrate that CDME induces greater that normal cystinotic levels in the mice.

TABLE 7

Results

| Animal (protocol) | Kidney Cystine Concentration (nmol cystine/ mg protein) | Liver Cystine Concentration (nmol cystine/ mg protein) |
|---|---|---|
| Mouse #1 (5,000 mg CDME/kg) | (205/6.8 =) 30 | (850/5.8 =) 150 |

TABLE 7-continued

Results

| Animal (protocol) | Kidney Cystine Concentration (nmol cystine/ mg protein) | Liver Cystine Concentration (nmol cystine/ mg protein) |
|---|---|---|
| Mouse #2 (5,000 mg CDME/kg) | (430/5.8 =) 74 | (1940/8.4 =) 230 |
| Mouse #3 (10,000 mg CDME/kg) | (930/9.6 =) 97 | (85/12.6 =) 6.7 |
| Control Mouse (black) (0 mg CDME/kg) | (8.0/6.5 =) 1.2 | Not determined |
| Control Mouse (heterozygous) (0 mg CDME/kg) | (1.8/5.1 =) 0.35 | Not determined |
| Control Mouse (wild-type) (0 mg CDME/kg) | (1.0/4.1 =) 0.24 | Not determined |

Example 6

Anticancer Effect of Compounds of the Formulae of the Invention in Nude Mice

Human breast cancer cells are transplanted in nude mice and tumor growth is induced for 2 to 3 weeks. Then, compounds of the invention are injected to the tumor tissue by the 4-3 days method, that is, injection for 4 days and rest for 3 days. PBS solution (50 μL) with or without a compound of the invention (20 μg) is injected to the tumor of treatment (T) or control (C) mice, respectively. The tumor volume is estimated in treatment and control mice by measuring both long and short diameters and compared in order to determine suppression and/or reduction of tumor.

All documents and public databases cited within this specification are incorporated herein by reference.

The invention claimed is:

1. A method of treating estrogen receptor-negative breast cancer in a mammalian subject, said method comprising administering cystine dimethyl ester or a pharmaceutically acceptable salt thereof to said mammalian subject.

2. The method according to claim 1, further comprising administering TNF-α.

3. The method according to claim 2, wherein TNF-α is administered prior to said cystine dimethyl ester.

4. The method according to claim 2, wherein TNF-α is administered concurrently with said cystine dimethyl ester.

5. The method according to claim 2, wherein TNF-α is administered subsequent to said cystine dimethyl ester.

6. The method according to claim 1, wherein said cystine dimethyl ester is administered in vivo.

7. The method according to claim 1, wherein said cystine dimethyl ester is administered ex vivo.

8. The method according to claim 1, wherein said administering comprises a route of administration selected from the group consisting of oral, topical, systemic, enteral, parenteral, intravenous, intramuscular, sub-cutaneous, intracutaneous, intraperitoneal, intra-portal, intra-prostatic, intra-arterial, intra-dermal, intra-thecal, intra-lesional, intra-tumoral, intra-bladder, intra-vaginal, intra-ocular, intra-rectal, intra-pulmonary, intra-spinal, transdermal, subdermal, regional perfusion at the site of a tumor, nasal inhalation, pulmonary inhalation, impression into skin and electroporation.

9. The method according to claim 1, wherein said cystine dimethyl ester is administered to said mammalian subject at a dosage of from 1.0 µg to 500 mg/kg subject body weight.

10. The method according to claim 1, wherein the cystine level in lysosomes of cells of said cancer are increased above 0.5 nmol/mg cell protein.

11. The method according to claim 1, wherein said cystine dimethyl ester is present in a composition comprising a pharmaceutically acceptable carrier.

\* \* \* \* \*